United States Patent [19]

Goetz

[11] 4,048,990
[45] Sept. 20, 1977

[54] HEART MASSAGE APPARATUS

[76] Inventor: Robert H. Goetz, 80 Vernon Drive, Scarsdale, N.Y. 10583

[21] Appl. No.: 724,456

[22] Filed: Sept. 17, 1976

[51] Int. Cl.² ............................................. A61H 7/00
[52] U.S. Cl. ...................................................... 128/64
[58] Field of Search ...................... 128/61, 64, 38–40, 128/24.1, 24.2, 24 R, 28

[56] References Cited

U.S. PATENT DOCUMENTS

| | | | |
|---|---|---|---|
| 2,826,193 | 3/1958 | Vineberg | 128/64 |
| 3,034,501 | 5/1962 | Hewson | 128/64 |
| 3,455,298 | 7/1969 | Anstadt | 128/64 |
| 3,478,737 | 11/1969 | Rassman | 128/64 |
| 3,496,932 | 2/1970 | Prisk et al. | 128/64 |
| 3,590,815 | 7/1971 | Schiff | 128/64 |

Primary Examiner—Lawrence W. Trapp
Attorney, Agent, or Firm—Stephen B. Judlowe; James M. Rhodes, Jr.

[57] ABSTRACT

An apparatus is herein described for directly massaging a human heart which apparatus can be left in place at the end of an operation and be removed at a later date. The apparatus generally includes a cup-like inflatable bladder formed to surround the heart and to massage the heart in a predetermined manner in response to the creation of pressure pulses within the bladder. A basket-like support is provided for disposing the bladder in an operational posture around a heart during the heart massaging process. In one form, the support is inflatable into a rigid structure and deflatable to a generally pliable, non-rigid condition to permit its removal through a small opening or a tube. In addition to the bladder and basket-like support means, a suction tube communicates with the annular space defined between the heart and the bladder so as to insure a positive contact between the bladder and the heart. After the heart massaging operation has been completed, and with the chest incision of the patient entirely closed, the bladder and support member may be deflated to the pliable condition, pulled from over the heart and removed through the small opening remaining from the generally closed incision or through a chest tube. Also, in case the heart stops after the chest has been closed, the apparatus, if left in place, can be activated without having to take the patient to the operating room for manual massage.

6 Claims, 7 Drawing Figures

HEART MASSAGE APPARATUS

BACKGROUND OF THE INVENTION

The present invention relates to medical implements and more specifically to an apparatus for directly massaging a patient's heart.

From time to time, in the practice of medical surgery, it becomes necessary to directly massage the heart of a patient. One method has been for the physician to take the heart in his hand and apply a massaging motion thereto. Although this method is effective, its effectiveness is limited to the physical stamina of the individual massaging who may become quite tired or even endure hand cramps after a long period of such massaging and, on occasions the squeezing fingers have been known to cause damage to the heart.

Therefore, apparatus has been developed for massaging a heart by applying pressure pulses to a bladder generally surrounding the heart which pressure is applied through tubes extending to a pressure source. The bladder of such an apparatus must be maintained in an operational posture by a collapsible, semi-rigid, basket-like support means. However, as is the case with hand massaging a patient's heart, the incision in the patient's chest must be left opened so as to permit the removal of the apparatus after the massaging operation has been completed. This, of course, means that the patient has to remain on the operating table.

It would therefore be advantageous if a heart massaging apparatus were provided which could be removed from over the patient's heart even after the incision in the patient's chest has been substantially closed.

OBJECTS AND SUMMARY OF THE PRESENT INVENTION

It is therefore an object of the present invention to provide an apparatus for directly massaging a patient's heart which apparatus may be removed after the incision in the patient's chest has been substantially closed.

This object is achieved by the provision of an inflatable bladder formed to surround a heart and operable to intermittently squeeze the heart in a massaging manner in response to the creation of predetermined pressure pulses within the bladder. An inflatable, basket-like bladder support is provided for disposing the bladder in an operational posture around the heart during the heart massaging operation. The support means is deflatable to a pliable, non-rigid condition after the heart massaging process is completed so that the overall apparatus may be removed through a small opening in the patient's chest after the patient's incision has been almost entirely closed.

DRAWINGS

While the invention is particularly pointed out and distinctly claimed in the concluding portion of the specification, a preferred embodiment is set forth in the following detailed description which may be best understood when read in connection with the accompanying drawings in which:

DETAILED DESCRIPTION

Figure 1:
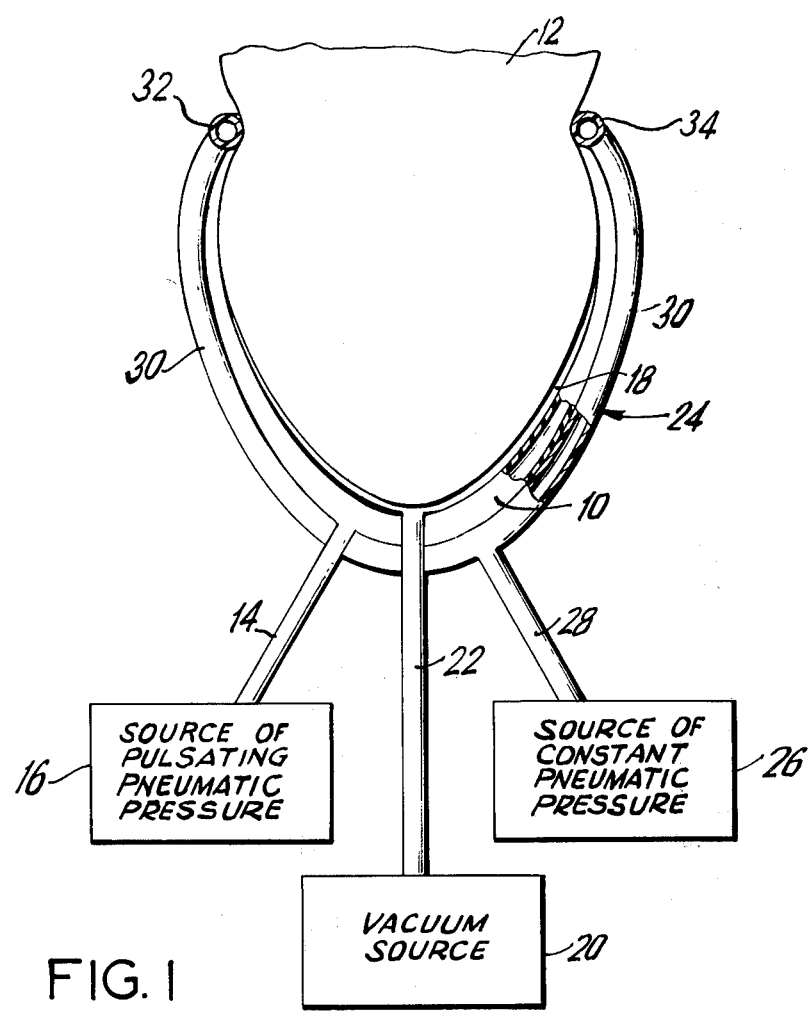
FIG. 1 is a diagrammatic representation of the apparatus according to the present invention.
Figure 6:
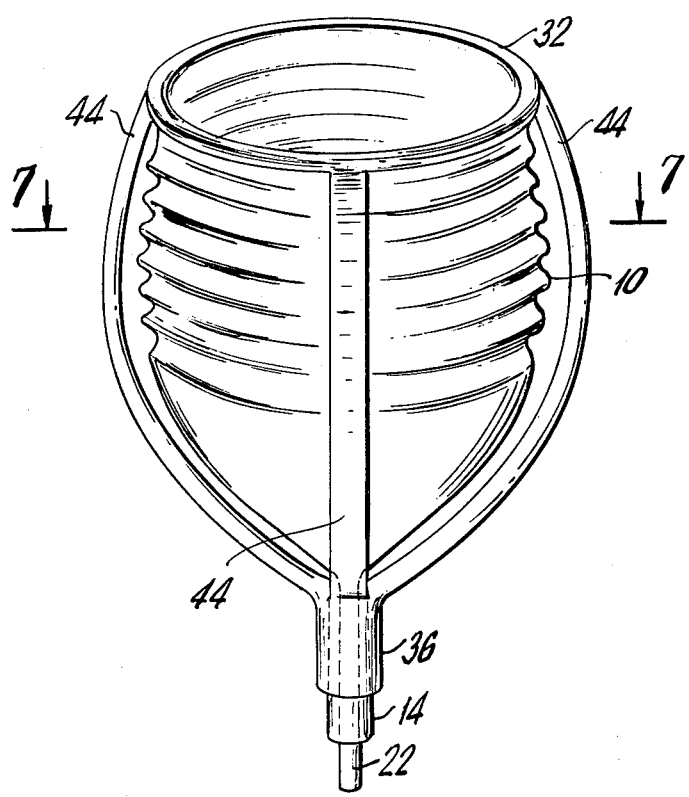
FIG. 6 is a perspective view of another form of the invention having collapsible, basket-like support means containing an inflatable heart massaging bladder.

Referring now to the drawings in which like numerals are used to indicate like parts throughout the various views thereof, FIG. 1 shows a heart massaging bladder 10 in an operational posture with respect to a patient's heart 12. In one form, the bladder 10 is generally cup-like in configuration and communicates through elongated tube 14 to a source of pulsating pneumatic pressure 16. In another form, the bladder 10 is cuff-like and communicates through separate channels to a source of pulsating pneumatic pressure as shown in FIG. 6. The bladder 10 is forced into positive contact with the heart 12 by the creation of a vacuum within the generally annular space 18 defined between the heart and the cup-like bladder 10. The vacuum is created by an evacuation source 20 communicating with the space 18 through an elongated tube 22.

Figure 2:
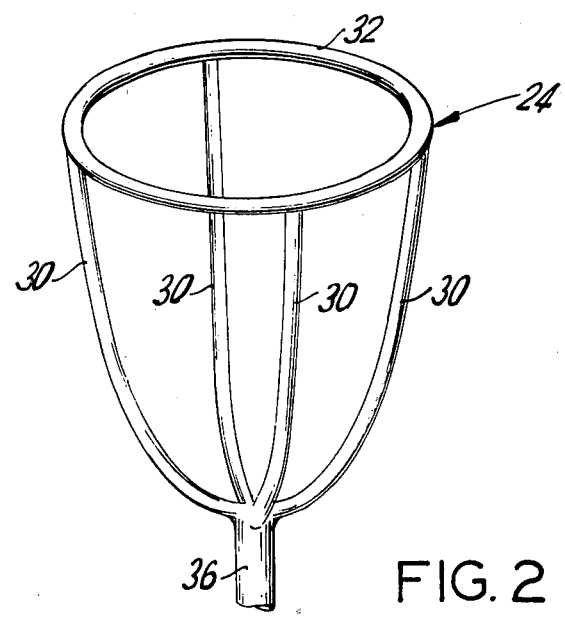
FIG. 2 is a perspective view of a basket-like supporting means according to the present invention.
Figure 3:
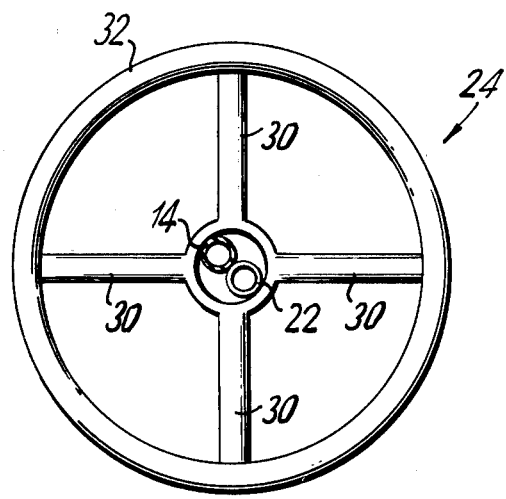
FIG. 3 is a top plan view of the basket-like support means of FIG. 2.

The bladder 10 is further supported by a basket-like support member 24 which, in one form, is inflatable into the rigid position shown in FIGS. 1-3. In another form, the support member may be formed by collapsible, semi-rigid, solid struts shown in FIGS. 6 and 7. The basket 24 may comprise any suitable rubber or plastic which stands rigid upon inflation and becomes pliable upon deflation. The support basket 24 is inflated by a source of constant pneumatic pressure 26 through an elongated tube 28. The basket 24 might also be made from a physiologically inert, semi-rigid material which, when properly manipulated, can assume a collapsed form. The basket 24 may be separate from or integrally formed with the bladder 10.

Figure 4:
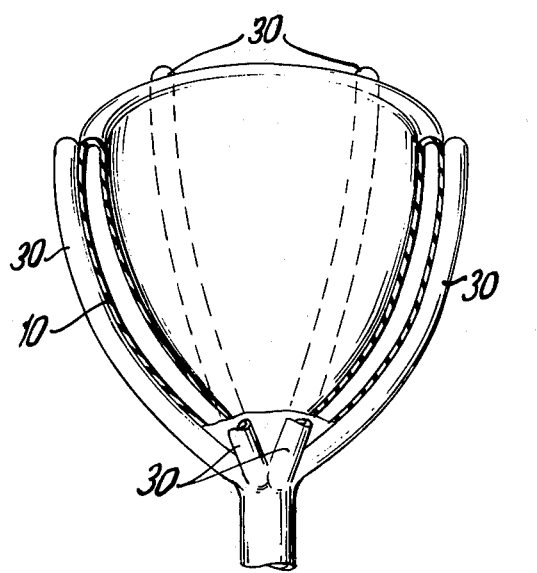
FIG. 4 is a generally perspective view of one form of the invention.

As can be seen by reference to FIG. 2, the basket-like support means may comprise a series of upwardly extending arms or struts 30 and an upper annular portion 32. As indicated in both FIGS. 1 and 2, the upper annular portion 32 may form somewhat of a bead 34 in cross section to facilitate the fitting of the overall apparatus around a heart to be massaged. Alternatively, the basket may be formed to present upwardly extending struts 30 without the annular portion 32 as shown in FIG. 4.

Figure 5:
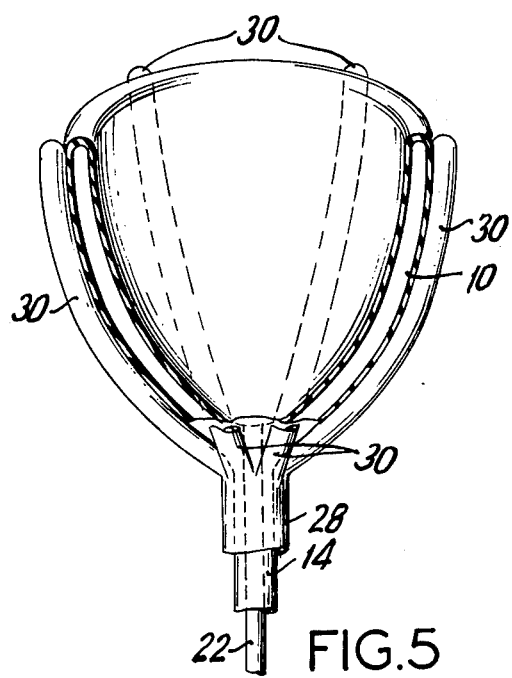
FIG. 5 is a generally perspective view of another form of the invention.

The lower stem 36 of the basket support member 24 may be formed rigid and the pulsating pneumatic pressure tube 14 and vacuum source evacuating tube 22 may be disposed within the tube 36 as depicted in FIGS. 5 and 6. Alternatively, the stem 36 and tube 28 may be flexible to facilitate the overall removal thereof from within the chest cavity of the patient.

In one form of the invention, the three tubes 14, 22 and 28 may be co-axial as shown in FIG. 5. Preferably, the vacuum tube 22 would comprise the innermost tube, the pulsating pressure tube 14 would be the intermediate tube and the constant pressure tube 28 would comprise the outermost tube. In an alternative form, illustrated by FIG. 6, the outer-most tube 36 is formed by a collapsible, solid, semi-rigid, inert material which forms the struts 44 and annular portion 32.

In operation, the basket-like support 24 is placed in rigid condition by inflation or simple elastic expansion of a collapsible semi-rigid material. The cup-like bladder 10 is positioned about a heart to be massaged. The vacuum source 20 is actuated to evacuate the annular space 18 and to draw the bladder 10 into intimate contact with the heart 12.

Figure 7:
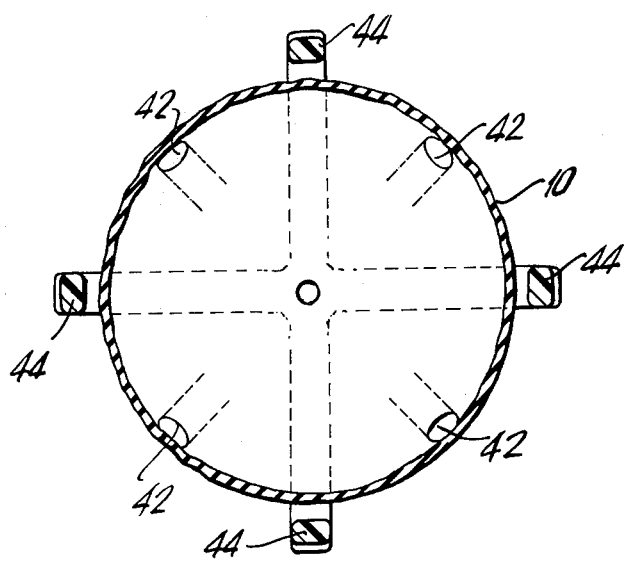
FIG. 7 is a cross-sectional view of the device taken along line 7—7 of FIG. 6.

FIG. 7, a cross sectional view along line 7—7, depicts the bladder 10 resting within a basket 24 formed by collapsible solid, semi-rigid supports 44 below the bladder, shown in phantom. The bladder can be inflated by means of channels 42, also shown in phantom. The wavy line depicting the top of the bladder 10 in FIG. 6 represents the top cuff of the bladder which encircles the heart.

After the bladder has been disposed in an operational posture about the heart, the bladder is then pulsated in a predetermined manner so as to effect the desired massaging action.

In the inflatable embodiment, when it is determined that the massaging apparatus is no longer necessary, the source of constant pneumatic pressure 26 is released from the support member 24 and the bladder 10 is deflated. Also, the vacuum source is removed. Whereupon, the overall apparatus deflates to a pliable, limp condition and may be readily pulled out through a very small opening in the patient's chest cavity which opening may remain after the overall incision has been substantially closed.

In this manner, the heart of a patient may be directly massaged even though his chest cavity has been closed and the patient is removed from the operating room to the recovery room or intensive care unit and is no longer anesthetized.

While what has been disclosed herein is a preferred embodiment of the present invention, it is to be understood that various modifications and changes may be made therein without departing from the invention. It is therefore intended to cover in the following claims all such modifications and changes as may fall within the true spirit and scope of the present invention.

What is claimed is:

1. Apparatus for directly massaging a patient's heart, comprising:
    a cup-like, inflatable bladder formed to surround a heart and operable to intermittently squeeze the heart in a massaging manner in response to the creation of predetermined pressure pulses within said bladder;
    a collapsible, basket-like, bladder support means for disposing said bladder in an operational posture around the heart during a heart massaging operation, said support means being erectible into a generally rigid, bladder supporting condition and being collapsible to a non-rigid, pliable condition;
    suction means for creating a predetermined vacuum in the generally annular space defined between said bladder and the heart when the bladder is disposed in an operational posture with respect to the heart; and
    said bladder and said support means being so formed that upon the collapse of said bladder and said support means, and upon the release of said suction means, the overall heart massaging apparatus collapses into non-rigid, pliable condition so that the overall apparatus may be safely pulled from over the heart and out through an opening defined by a generally closed incision in the patient, such opening being several times smaller than the transverse thickness of said basket-like supporting means when said last mentioned means is erected in an operational posture.

2. An apparatus according to claim 1, wherein:
    said inflatable bladder is adapted for connection with a source of pulsating pneumatic pressure.

3. An apparatus according to claim 2, wherein:
    said basket-like, support means is formed by an inflatable material and is adapted for connection with a source of constant pneumatic pressure.

4. An apparatus according to claim 3, wherein:
    said suction means includes an air evacuation source communicating with said annular space about said heart through a first elongated tube; said inflatable, basket-like support means communicates with said source of constant pneumatic pressure through a second elongated tube; said inflatable bladder means communicates with said source of pulsating pneumatic pressure through a third elongated tube; and
    whereby said overall apparatus may be pulled from over a heart upon the deflation of said bladder means and said supporting means and after the release of said suction means by pulling at least one of said first, second and third elongated tubes longitudinally out through an opening in the patient defined by a generally closed incision.

5. Apparatus according to claim 4, wherein at least one of said first, second and third elongated tubes are disposed concentrically with respect to each other.

6. Apparatus according to claim 4, wherein at least one of said first, second and third elongated tubes is of a rigid structure.

* * * * *